US009020156B2

(12) United States Patent
Dantele et al.

(10) Patent No.: US 9,020,156 B2

(45) Date of Patent: Apr. 28, 2015

(54) METHOD FOR REDUCING THE NOISE EMISSION OF A TRANSFORMER

(75) Inventors: Andreas Dantele, Steyr (AT); Alexander Hackl, Machtrenk (AT); Johannes Korak, Steyr (AT); Thomas Rittenschober, Linz (AT); Helmut Wernick, Linz (AT)

(73) Assignee: Siemens Aktiengesellschaft, München (DE)

( * ) Notice: Subject to any disclaimer, the term of this patent is extended or adjusted under 35 U.S.C. 154(b) by 746 days.

(21) Appl. No.: 13/386,672

(22) PCT Filed: Jul. 24, 2009

(86) PCT No.: PCT/EP2009/059557

§ 371 (c)(1), (2), (4) Date: Jan. 24, 2012

(87) PCT Pub. No.: WO2011/009491

PCT Pub. Date: Jan. 27, 2011

(65) Prior Publication Data

US 2012/0121101 A1 May 17, 2012

(51) Int. Cl.

*A61F 11/06* (2006.01)
*H01F 27/33* (2006.01)
*G10K 11/178* (2006.01)

(52) U.S. Cl.

CPC .............. *H01F 27/33* (2013.01); *G10K 11/178* (2013.01)

(58) Field of Classification Search

USPC ................ 381/71.1–71.13, 71.7–71.9, 71.14; 700/28, 45

See application file for complete search history.

(56) References Cited

U.S. PATENT DOCUMENTS

| | | | | |
|---|---|---|---|---|
| 5,617,479 | A | 4/1997 | Hildebrand | |
| 5,692,053 | A | 11/1997 | Fuller | |
| 2006/0064180 | A1 * | 3/2006 | Kelkar et al. | 700/28 |

* cited by examiner

*Primary Examiner* — Xu Mei
*Assistant Examiner* — Friedrich W Fahnert

(57) ABSTRACT

A method for reducing the noise emission of a transformer, the transformer tank of which is filled with liquid and the tank wall of which vibrates during operation, is provided. The method is characterized by the sequence of the following method steps: detecting natural frequency values of the tank wall for at least one excitation frequency; determining at least one eigenmode for which the vibration of the tank wall is composed at an excitation frequency, from the natural frequency values, wherein areas of large curvature are determined on the tank wall; arranging at least one vibration loading device in at least one of said areas; and controlling the at least one vibration loading device by means of a control device in order to counteract the vibration of the tank wall.

8 Claims, 4 Drawing Sheets

1

2

3

4

5
f

FIG 2A
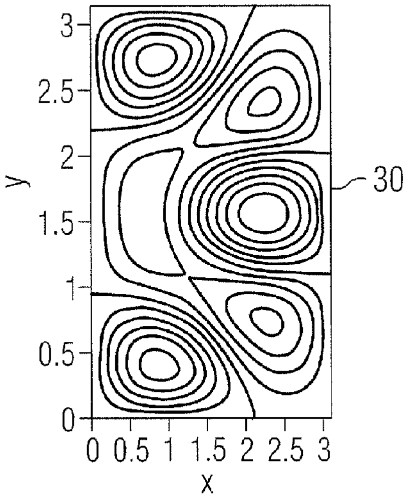
FIG 2B
FIG 2C
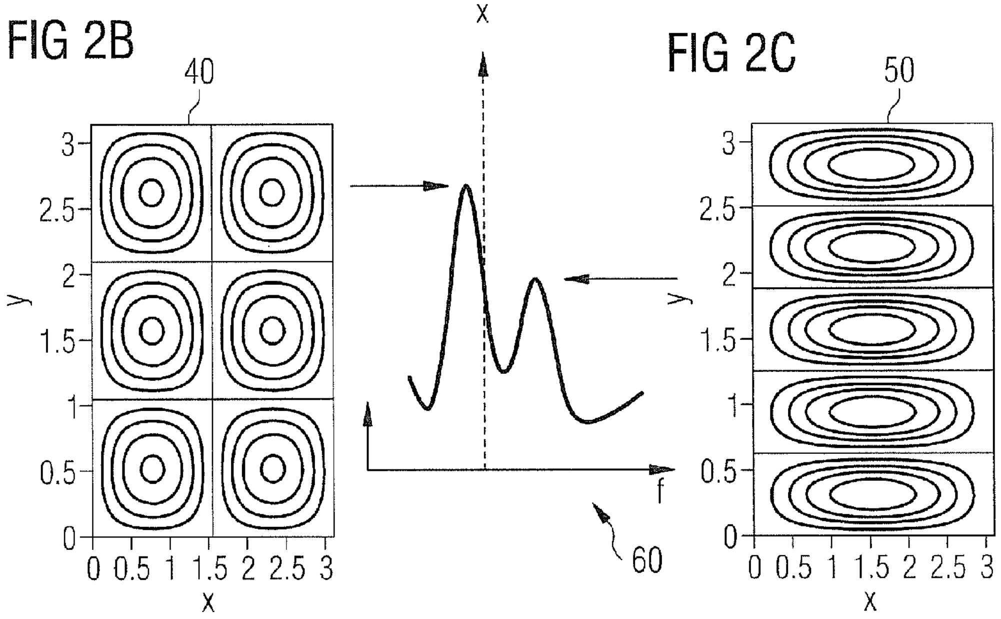

METHOD FOR REDUCING THE NOISE EMISSION OF A TRANSFORMER

CROSS REFERENCE TO RELATED APPLICATIONS

This application is the US National Stage of International Application No. PCT/EP2009/059557, filed Jul. 24, 2009 and claims the benefit thereof. All of the applications are incorporated by reference herein in their entirety.

TECHNICAL FIELD

The invention relates to a method for reducing the noise emission of a transformer, the transformer tank of which is filled with a liquid and the tank wall of which vibrates during operation.

PRIOR ART

During operation of a transformer, the deformation of the soft magnetic core due to magnetostriction and/or the electromagnetic forces acting on the windings result in pressure waves in the cooling liquid of the transformer, wherein said pressure waves cause the wall of the transformer tank to vibrate. These tank vibrations result in acoustic radiation which is in the audible range and perceived in particular as a nuisance if the transformer is installed in the vicinity of a residential area, for example.

Various devices that actively work to reduce operating noises of a transformer are known. For example, DE 699 01 596 T2 discloses a low-noise transformer in which a vibration cell is arranged in the transformer tank and generates an opposite-phase vibration to the pressure waves, thereby moderating the vibrations of the tank wall. A similar method is proposed in U.S. Pat. No. 5,394,376, in which a liquid displacement device likewise counteracts pressure waves in the interior of the transformer tank.

However, these known devices share the characteristic that a connection is required between an actuator and the liquid in the interior of the tank. Furthermore, the actuator consumes a significant amount of energy.

STATEMENT OF THE INVENTION

The present invention addresses the problem of specifying a method which effectively reduces the noise emission of a transformer in a manner which is as simple and reliable as possible, while consuming as little energy as possible.

This problem is solved by a method having the features in the claims. Advantageous embodiments are defined in the subclaims.

According to a fundamental idea of the invention, a vibration loading device working in opposite phase to the vibration is arranged externally on the wall of the transformer tank in such a way that it lies as closely as possible to areas of maximal curvature or maximal transverse deflection of an eigenform of the tank wall. It is thus possible efficiently to influence the unwanted vibration of the tank wall. An eigenform, also called a mode, describes the appearance of a vibration form at a natural frequency. At each natural frequency, the tank wall vibration has a specific geometric form, i.e. a specific mode. In a first approximation, a tank wall can be considered as a plate with a fixed edge. The plate modes occurring there are denoted by an ordinal number (m-n). If the vibration loading device, also referred to as an actuator in the following, is placed in an area of significant deflection of the eigenform, comparatively little energy is required to absorb the vibration.

A particularly beneficial embodiment of the inventive method is characterized in that a piezoelectric element is used as a vibration loading device. This piezoelectric element has the particular advantage that it can be used as both an actuator and a measuring transducer. According to the invention, provision is made for the piezoelectric element or another measuring transducer to supply a measured signal that is proportional to the vibration of the tank wall, and for said measured signal to be returned to the control device. The control device analyzes said measured signal and, on this basis, determines amplitude and phase for a control signal which is used to activate the piezoelectric actuator for absorbing the vibration. In this way, the vibration damping can be adapted to changes in operating status. The effect of the noise reduction is therefore maintained over a long period of operation.

BRIEF DESCRIPTION OF THE DRAWINGS

In order to explain the invention further, the following part of the description refers to the drawings, which contain further advantageous embodiments, details and developments of the invention, and in which:

FIG. 2 shows an illustration of simulation images showing the breakdown of a plate vibration into its eigenforms;

EMBODIMENT OF THE INVENTION

Figures 1A, 1B, 1C, 1D, 1E:
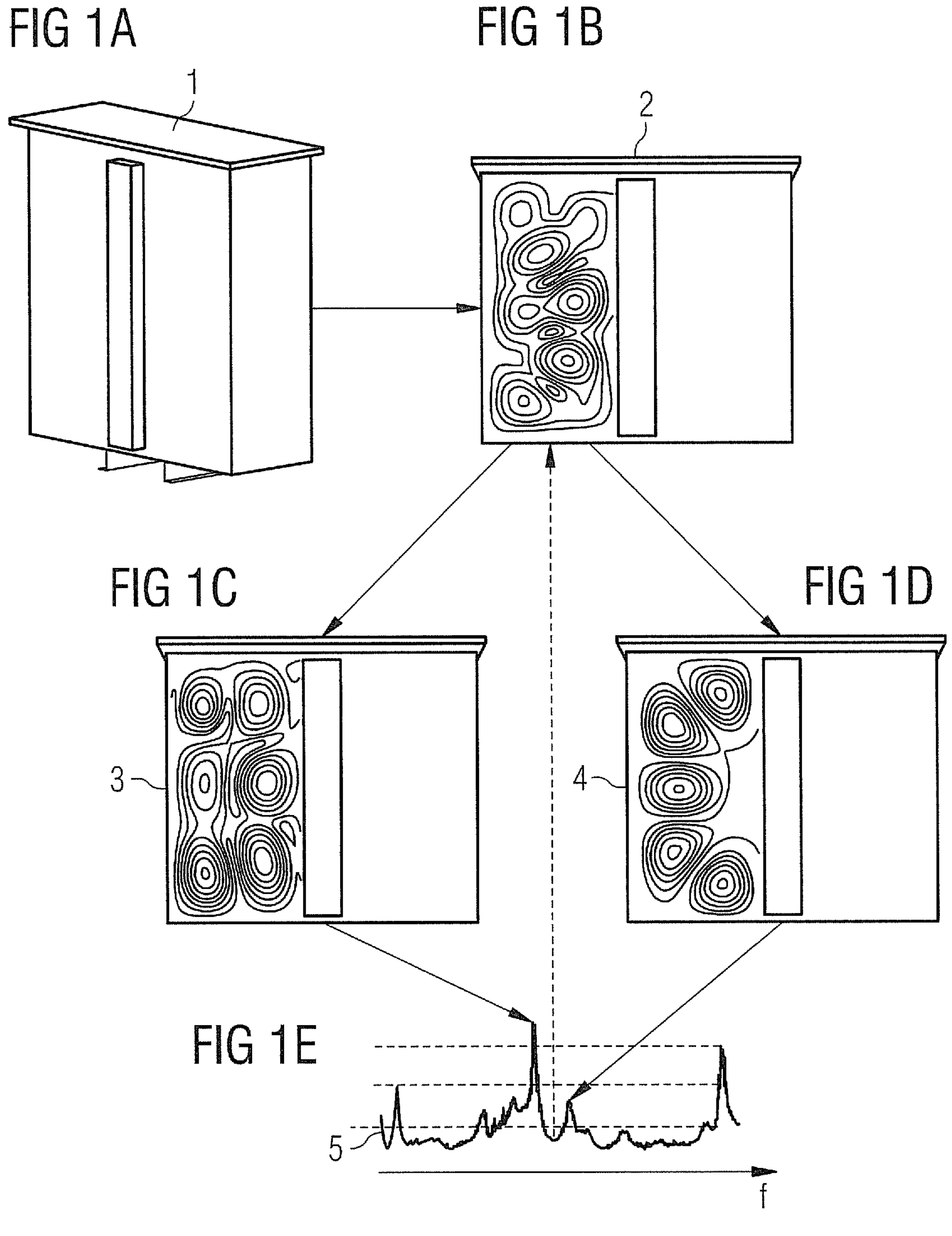
FIG. 1 shows tank vibration as a result of an excitation of 100 Hz, and a breakdown of said tank vibration into eigenforms.
Figure 3B:
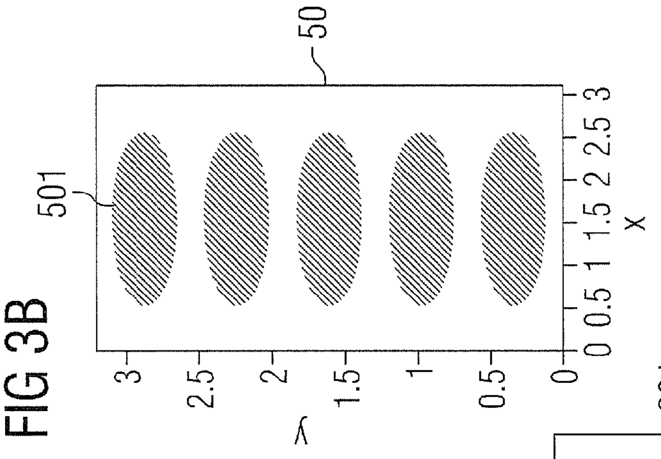
FIG. 3 shows an illustration of simulation images showing a superimposition of a 2-3 mode with a 1-5 mode.
Figure 3D:
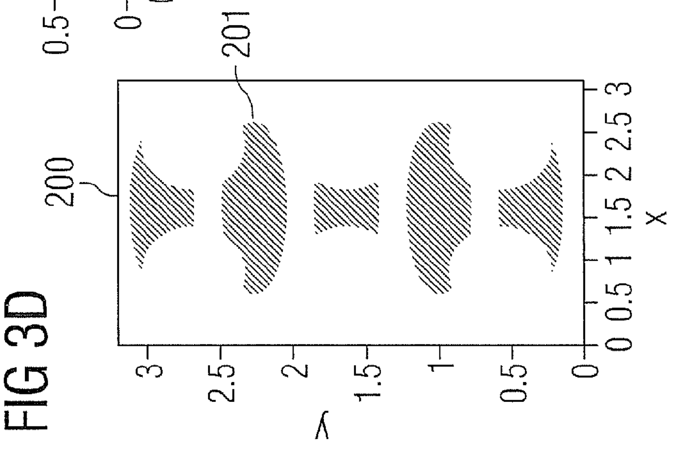
Figure 3C:
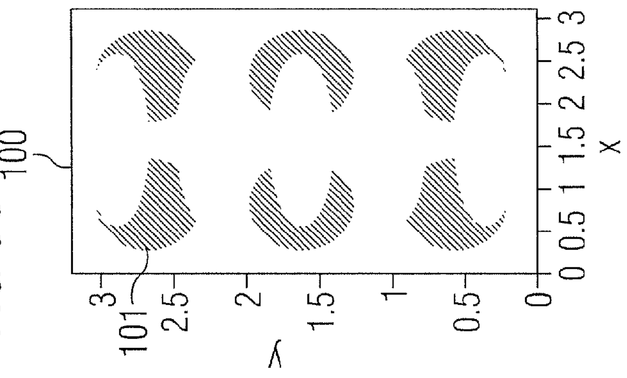
Figure 3A:
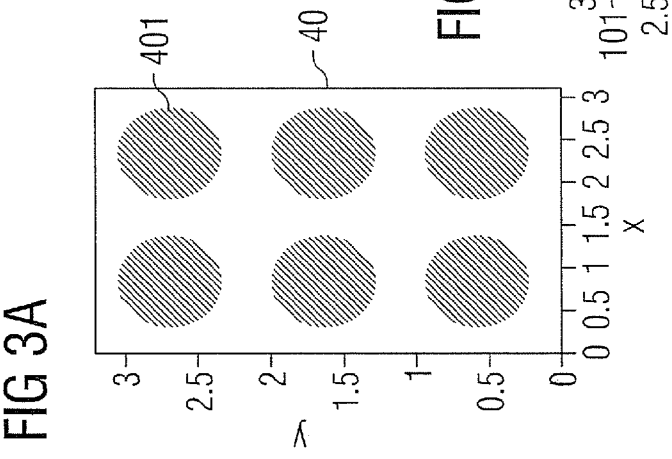

FIG. 1*a* shows a three-dimensional illustration of a transformer tank. As described in the introduction, the tank wall of the transformer is caused to vibrate by the transformer core and/or the transformer winding during operation. This noise radiation is a nuisance, particularly in the case of high-power transformers. In the case of distribution transformers or power transformers, the excitation frequency is normally 50 Hz or 60 Hz.

FIG. 1*b* illustrates the vibration form that develops on the wall of the transformer tank. Such a pictorial illustration of a tank vibration form can be obtained experimentally by analyzing the vibration during operation. FIGS. 1*b*, 1*c* and 1*d* describe the speed of the tank surface in each case, i.e. the speed of oscillation of the wall relative to its position of rest. The regions of maximal deflection (bulge) and the regions of minimal deflection (edges) can be seen from the illustration.

FIG. 1*e* illustrates the mode spectrum. Devices and methods for creating a mode spectrum are known to a person skilled in the art. A container wall can be caused to vibrate by means of a pulse hammer, for example, and the vibrations of the tank wall can be measured by acceleration sensors or by piezoelectric force transducers that are distributed over the surface of the tank wall, for example. These measured signals can be forwarded to a computer system which performs a modal analysis and numerically determines the dynamic characteristics of the tank wall therefrom.

As illustrated above, a vibration form is composed of the interference of its natural vibration forms and can therefore be broken down into its modes. This can be done by means of a simulation, for example. FIG. 1 shows an analysis of a 100-Hz tank vibration as a result of a simulation on a computer system. The eigenforms are illustrated in the simulation images shown in FIGS. 1*c* and 1*d*. It is evident from FIGS. 1*c* and 1*d* that the tank vibration is essentially composed of two natural vibration forms: a 2-3 mode (see FIG. 2*b*) and a 1-5 mode (see FIG. 2*c*). This composition of the tank vibration is also illustrated by the diagram in FIG. 1*e*, which shows the portion of the amplitude of the modes of tank vibration as a function of the frequency. The vertical dotted line identifies the excitation frequency of 100 Hz. The peak to the left of this shows the more distinctive extreme value of the 2-3 mode at its associated natural frequency of 99 Hz. The peak to the right of this shows the extreme value of the 1-5 mode at its associated natural frequency of 101 Hz.

The upper simulation image in FIG. 2 shows the vibration form 30; the lower two simulation images 40 and 50 respectively show the 2-3 mode (FIG. 2*b*) and the 1-5 mode (FIG. 2*c*). The amplitude is again indicated as a function of the frequency in the diagram 60 in the center of FIG. 2.

Noise reduction aims to achieve the greatest possible effect in terms of a decrease in noise, using the fewest possible actuators. In order to reduce the tank vibration, it is necessary to attach at least one actuator per mode. In order to discover those areas on the tank surface which are particularly suitable for absorption of the vibration, vibration images are superimposed. In this case, it must be ensured that one mode is damped without the other mode being unintentionally excited. In order to discover these areas on the tank surface, a subtraction of the mode images is performed according to the invention, this being explained in greater detail below:

FIG. 3 shows a 2-3 mode in the vibration image 40. Regions in which this 2-3 mode can be excited and therefore damped particularly effectively are identified by the reference sign 401 and shown by gray shading in the drawing. The 1-5 mode 50 that is illustrated on the right-hand side can be excited particularly effectively in the areas 501. The white areas in the two images 40, 50 identify regions in which the respective mode can only be excited slightly. In order now to bring about an efficient reduction of the noise using the fewest possible actuators, the gray shaded areas of the 1-5 mode (FIG. 3*b*) are subtracted from the gray shaded areas of the 2-3 mode (FIG. 3*a*). The result is illustrated in FIG. 3*c* (image 100). The difference areas 101 represent regions on the tank wall which are particularly suitable for effectively damping one of the two modes, without the other mode being unintentionally excited. FIG. 3*c* shows sickle-shaped and drop-shaped residual areas, in which it is possible to arrange an actuator that effectively damps the 2-3 mode by introducing opposite-phase vibration, without thereby amplifying the 1-5 mode. Conversely, subtracting the gray areas 401 from the gray areas 501 (see FIG. 3*d* image 200) reveals those regions 201 in which the mode 1-5 can be excited effectively, but the mode 2-3 only slightly.

Those areas on the tank wall in which vibrations can be damped particularly efficiently are thus determined.

It is essentially intended to damp as many frequencies and modes as possible using the fewest possible actuators. In addition to the dominant excitation, however, the higher harmonics of the dominant excitation are also unwanted.

Figure 4:
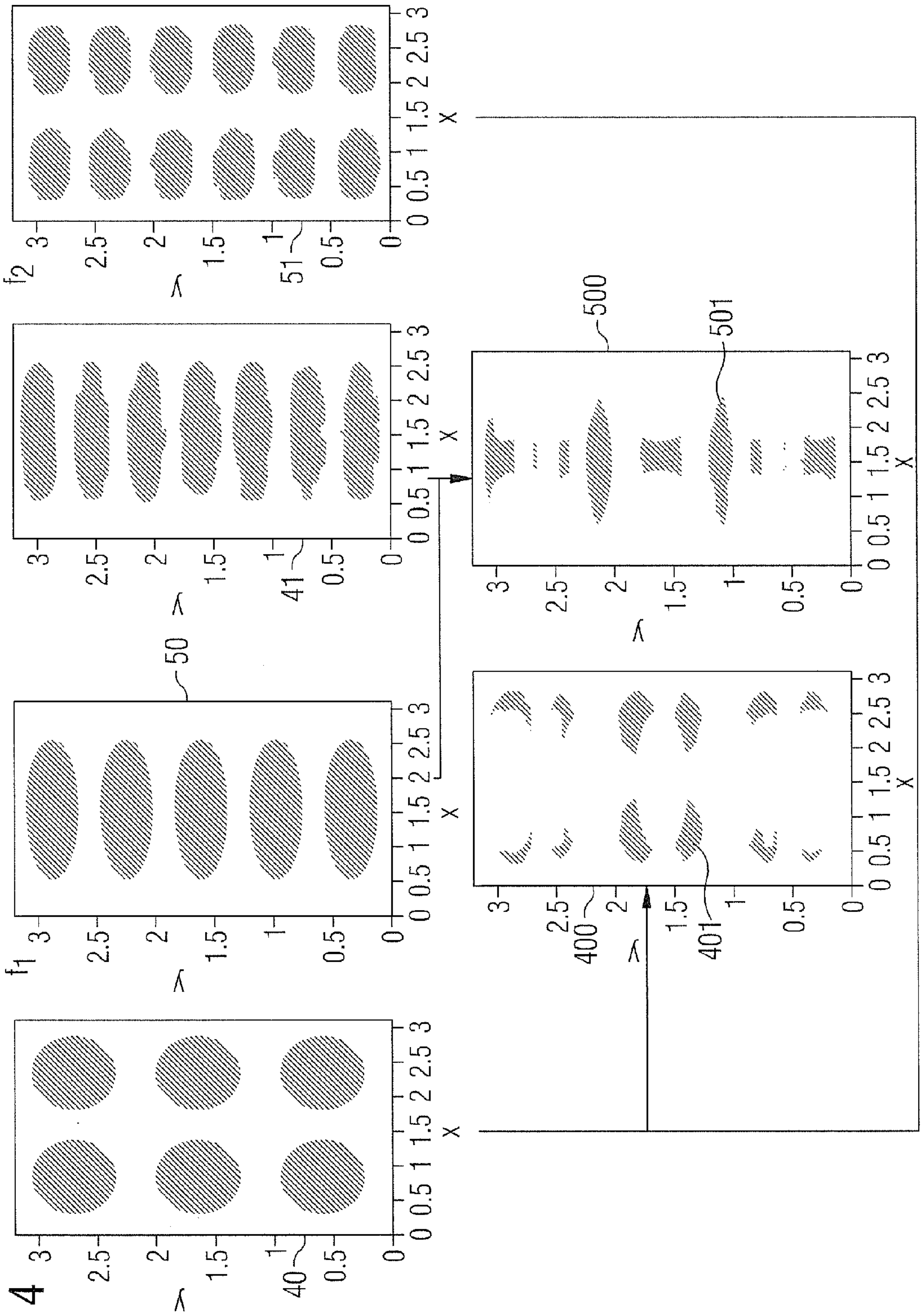
FIG. 4 shows an illustration of simulation images showing a superimposition of a 2-3 mode with a 2-6 mode and a superimposition of a 1-5 mode with a 1-7 mode.

FIG. 4 shows an illustration of simulation images assuming an excitation frequency of 100 Hz ($f_1$) and the first harmonic at 200 Hz ($f_2$). The tank vibration at 200 Hz is composed of a 1-7 mode (vibration image 41) and a 2-6 mode (vibration image 51).

In the superimposition image 400, the gray areas of the eigenforms 40 and 51 have been combined and the gray areas of the eigenform 50 have been subtracted. The areas 401 identify those areas in which the eigenforms 40 and 51 can be separately damped, ideally by means of an actuator.

In the superimposition image 500, the gray areas of the eigenform is 50 and 41 have been combined and the gray areas of the eigenform 51 have been subtracted. The gray shaded areas 501 identify those areas in which the eigenforms 50 and 41 can be separately damped, ideally by means of an actuator.

If an actuator is activated using a frequency mixture of 100 Hz and 200 Hz, it can be used to reduce both the 100 Hz component and the 200 Hz component. Using two actuators, it is therefore possible to damp two frequencies and four modes. In order to reduce the number of actuators, therefore, instead of considering every exciting frequency 100 Hz, 200 Hz, 300 Hz, 400 Hz, etc. individually, all of the relevant eigenforms of all frequencies are overlaid and those regions corresponding to the optimization strategy illustrated above are determined by means of superimposition. In this case, the number of actuators is progressively increased until all of the eigenforms can be corrected separately.

Although the tank is excited using the frequency of 100 Hz, the contribution of the natural vibration forms from which the tank vibration is composed fluctuates in amplitude and phase depending on operating status and operating time. In order to achieve an effective suppression of the acoustic radiation over the entire period of operation, the noise suppression system must be adapted to the current status. This is achieved by using the piezoelectric elements as vibration absorbers at some times and as measuring transducers for picking up a vibration at other times. In this measurement phase, the measured signal that is generated by the piezoelectric element is routed back to the control unit. On the basis of the measured signal, magnitude and phase of the measured vibration are determined in the control unit. The tank vibration is broken down into its eigenforms. When the piezoelectric element is used as a vibration absorber again, this information is used for the activation of the piezoelectric element or of other actuators if applicable. Each actuator is assigned a dedicated control circuit in this case. In this way, the suppression of the acoustic radiation is adapted. Each actuator is therefore adapted to the temporal changes of the tank vibration within its effective area. The effect of the noise reduction overall is therefore maintained over a long operating period.

The invention claimed is:

1. A method for reducing the noise emission of a transformer, the transformer tank of which is filled with a liquid and the tank wall of which vibrates during operation, comprising:

- detecting natural vibration values of the tank wall for at least one excitation frequency;
- determining at least two eigenforms, from which the vibration of the tank wall is composed at an excitation frequency, by means of computer-aided processing of the natural vibration values, wherein areas of maximal curvature of the tank wall are determined on the tank wall in each case by means of computer-aided superimposition of these at least two eigenforms;
- arranging a vibration loading device in at least one of these areas; and
- activating the vibration loading device by means of a control device in order to counteract the vibration of the tank wall.

2. The method as claimed in claim 1, wherein a subtraction of the at least two eigenforms is performed in the superimposition.

3. The method as claimed in claim 1, wherein the activation is performed such that each eigenform is counteracted separately.

4. The method as claimed in claim 3, wherein the activation is effected by a control signal which is composed of a frequency mixture in order to damp a plurality of eigenforms using different excitation frequencies.

5. The method as claimed in claim 3, wherein the vibration loading device is a piezoelectric element.

6. The method as claimed in claim 5, wherein a measuring transducer converts the vibrations of the tank wall into a measured signal that is supplied to the control device.

7. The method as claimed in claim 6, wherein the control device determines magnitude and phase of an eigenform from the supplied measured signal and, on the basis of these, calculates a control variable for a piezoelectric actuator, said control variable being used for the activation of the piezoelectric element in a time interval following the measurement interval.

8. The method as claimed in claim 5, wherein the piezoelectric element is fastened to the tank wall by means of an adhesive.

* * * * *